(12) United States Patent
Huang et al.

(10) Patent No.: US 7,820,716 B2
(45) Date of Patent: Oct. 26, 2010

(54) CRYSTALLINE POLYMORPHS OF DESVENLAFAXINE SUCCINATE AND THEIR PREPARATIONS

(75) Inventors: Cai Gu Huang, Guangzhou (CN); Hui Min He Huang, Guangzhou (CN)

(73) Assignee: Mai De Ltd, Marlborough, MA (US)

( * ) Notice: Subject to any disclaimer, the term of this patent is extended or adjusted under 35 U.S.C. 154(b) by 501 days.

(21) Appl. No.: 11/982,622

(22) Filed: Nov. 5, 2007

(65) Prior Publication Data

US 2008/0188567 A1 Aug. 7, 2008

Related U.S. Application Data

(60) Provisional application No. 60/878,983, filed on Jan. 8, 2007.

(51) Int. Cl.
*A61K 31/205* (2006.01)
*C07C 55/10* (2006.01)

(52) U.S. Cl. ...................................... 514/554; 562/590
(58) Field of Classification Search ....................... None
See application file for complete search history.

(56) References Cited

U.S. PATENT DOCUMENTS 6,673,838 B2 1/2004 Hadfield et al.

*Primary Examiner*—Paul A Zucker

(57) ABSTRACT

The present invention is directed to two new polymorph Form V and Form F of desvenlafaxine succinate, to processes of their preparations, pharmaceutical composition comprising such materials and their use in therapy. Form V is prepared from recrystallizing desvenlafaxine succinate in a mixture of tetrahydrofuran and ethanol. Form F is obtained from recrystallization of desvenlafaxine succinate in a mixture of cyclohexane and polar solvents such as ethanol, THF, methanol or isopropyl alcohol.

21 Claims, 11 Drawing Sheets

CRYSTALLINE POLYMORPHS OF DESVENLAFAXINE SUCCINATE AND THEIR PREPARATIONS

Figure 1:
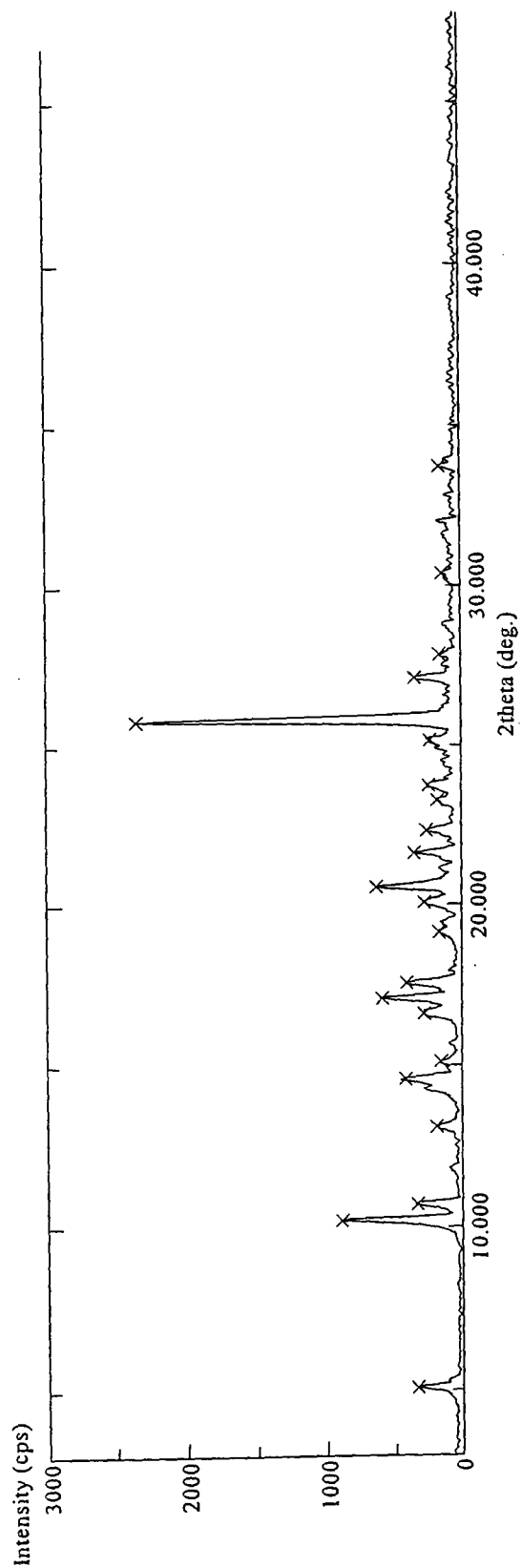

This application claims the benefit of priority to U.S. Provisional Patent Application Ser. No. 60/878,983 filed on Jan. 8, 2007, the disclosure of which is hereby incorporated by reference.

FIELD OF THE INVENTION

The present invention relates to two novel crystalline polymorphic forms of desvenlafaxine succinate, to processes for their preparations, pharmaceutical composition comprising such materials and their use in therapy.

BACKGROUND OF THE INVENTION

Desvenlafaxine succinate, its chemical name is (1-[2-(dimethylamino)-1-(4-phenol)ethyl]-cyclohexanol succinate, has the following structural formula:

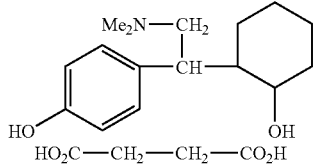

Desvenlafaxine succinate, also called as O-desmethyl venlafaxine succinate, is a succinate salt of O-desmethyl venlafaxine, which is a major metabolite of venlafaxine, and has been shown to inhibit norepinephrine and serotonin uptake. Synthesis of desvenlafaxine and its various salts have been disclosed in several publications (U.S. Pat. No. 4,535,186, WO 00/76955, U.S. Pat. Nos. 6,197,828, 6,689,912, 6,673,838 and 7,026,508).

U.S. Pat. No. 6,673,838 discloses four crystalline polymorphic forms (Form I, Form II, Form III and Form IV) and amorphous form of desvenlafaxine succinate.

New crystalline polymorph of a drug substance may display different melting point, hygroscopicity, stability, solubility and/or dissolution rate, crystallinity, crystal habits, bioavailability and formulation handling characteristics, which are among the numerous properties that need to be considered in preparing medicament that can be effectively administered. Therefore, the regulatory agencies require a definitive control of polymorphic form of the active component in solid pharmaceutical dosage forms.

Accordingly, there is an ongoing need to search new polymorphic forms of desvenlafaxine succinate that have better thermal stability and material flow character, lower water contents, and offer advantages for preparing reproducible pharmaceutical formulations. The novel and new polymorphic forms of desvenlafaxine succinate in the present invention help fulfill this and other needs.

SUMMARY OF THE INVENTION

The inventors have now surprisingly discovered two novel crystalline polymorphic forms (termed as Form V and Form F in the present invention) of desvenlafaxine succinate, which are more thermodynamically stable and particularly suitable for bulk preparation, handling and formulation advantages. Therefore, the current invention is generally directed to two novel polymorphic forms, namely Form V and Form F, of desvenlafaxine succinate. Additionally, efficient, economical and reproducible processes are found for the preparation of Form V, Form F, Form I and Form II of desvenlafaxine succinate.

Thus as a first aspect, the present invention provides a novel polymorphic form (Form V) of (1-[2-(dimethylamino)-1-(4-phenol)ethyl]-cyclohexanol succinate (desvenlafaxine succinate).

In another aspect, the present invention provides a process for preparing novel polymorph Form V of desvenlafaxine succinate by recrystallization of desvenlafaxine succinate in a mixture of heated tetrahydrofuran and one or more of any C1-C4 (one to four carbons) alcohols followed by isolating and drying the product.

In a still aspect, the present invention provides another novel polymorphic form (Form F) of (1-[2-(dimethylamino)-1-(4-phenol)ethyl]-cyclohexanol succinate (desvenlafaxine succinate).

In another aspect, the present invention provides a composition comprising (a) polymorph Form V or Form F of desvenlafaxine succinate and (b) a crystalline, hydrate, solvate, amorphous, polymorph Form I, Form II, Form III, Form VI or other polymorphic forms of desvenlafaxine succinate other than Form V or Form F, wherein the total weight of desvenlafaxine succinate in the composition is the sum of (a) and (b).

In a further aspect, the present invention provides processes for preparing novel polymorph Form F of desvenlafaxine succinate by recrystallization of desvenlafaxine succinate in any mixture of heated cyclohexane and one or more polar or non-polar organic solvents or combinations thereof followed by isolating and drying the product.

In a still further aspect, the present invention provides processes for preparing novel polymorph Form F of desvenlafaxine succinate by recrystallization of desvenlafaxine succinate in a mixture of heated organic solvents comprising 1,2-dichloroethane and one or more polar solvents or their combinations thereof followed by isolating and drying the product.

In a yet another aspect, the present invention provides processes for preparing Form I of desvenlafaxine succinate by recrystallization of desvenlafaxine succinate in a mixture of heated dichloromethane and methanol followed by isolating and drying the product.

In a further aspect, the present invention provides processes for preparing Form II of desvenlafaxine succinate by recrystallization of desvenlafaxine succinate in a heated isopropyl alcohol or acetonitrile, or a mixture of dichloromethane and ethanol followed by isolating and drying the product.

In another aspect, the present invention accordingly provides a pharmaceutical composition comprising Form V or Form F of desvenlafaxine succinate and one or more pharmaceutically acceptable diluents or carriers and, optionally, one or more other physiologically active agents.

In a still aspect, the present invention provides a method for the use of Form V or Form F of desvenlafaxine succinate for the treatment and/or prophylaxis of patients suffering from depression (e.g., major depressive disorder, bipolar disorder, and dysthymia), anxiety, panic disorder, generalized anxiety disorder, post traumatic stress disorder, premenstrual dysphoric disorder, fibromyalgia, agoraphobia, attention deficit disorder, obsessive compulsive disorder (including trichotillomania), social anxiety disorder, schizophrenia, obesity, anorexia nervosa, vasomotor flushing, cocaine and alcohol addiction, borderline personality disorder, cognitive enhancement, cognitive impairment, and cessation of smoking or other tobacco uses and certain complications thereof.

BRIEF DESCRIPTION OF THE ACCOMPANYING DRAWINGS

FIG. 1: X-ray powder diffraction (X-RPD) pattern of Form V of desvenlafaxine succinate prepared in Example 1.

Figure 2:
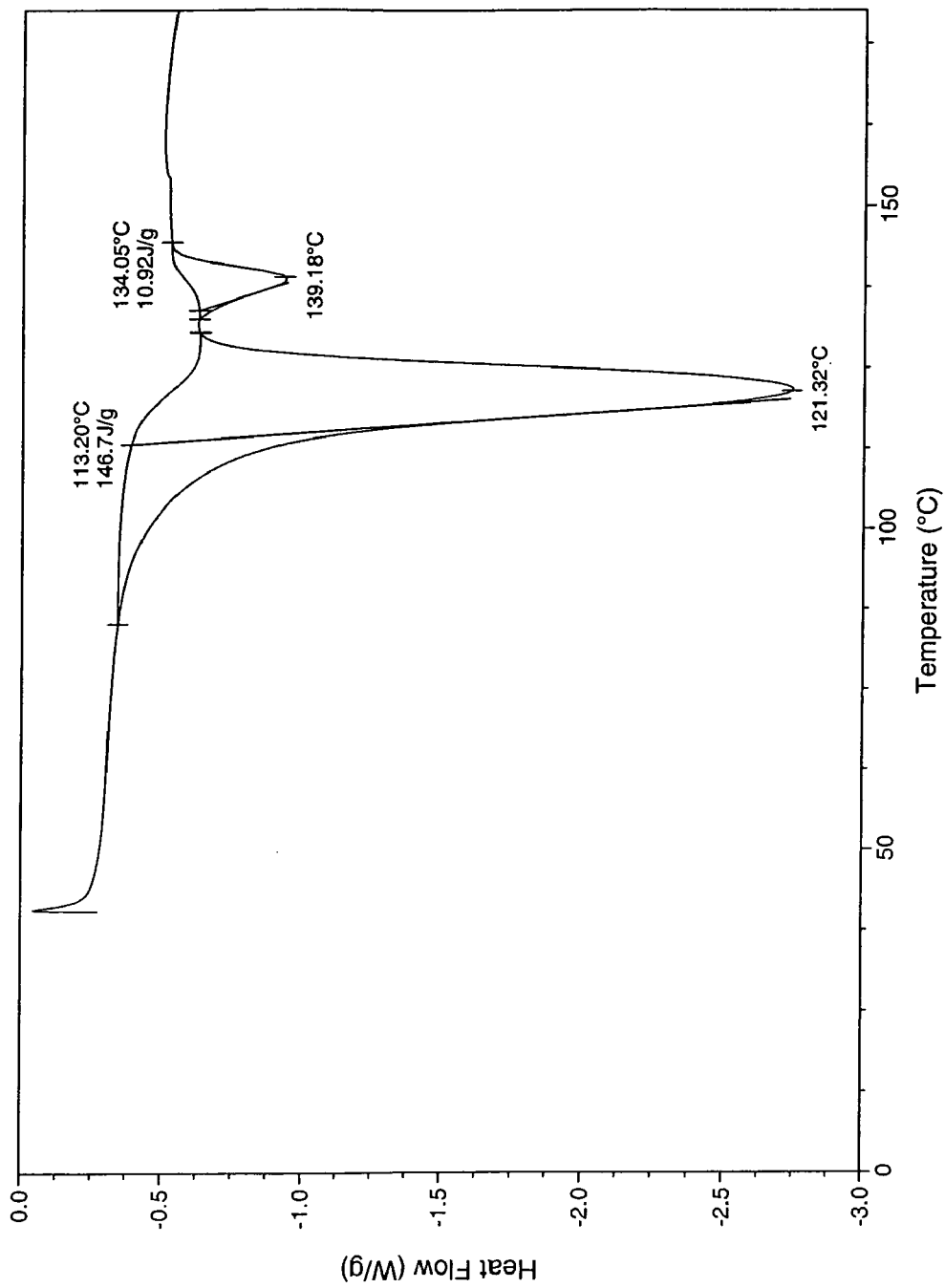

FIG. 2: Differential scanning calorimetry (DSC) of Form V of desvenlafaxine succinate obtained prepared in Example 1.

Figure 3:
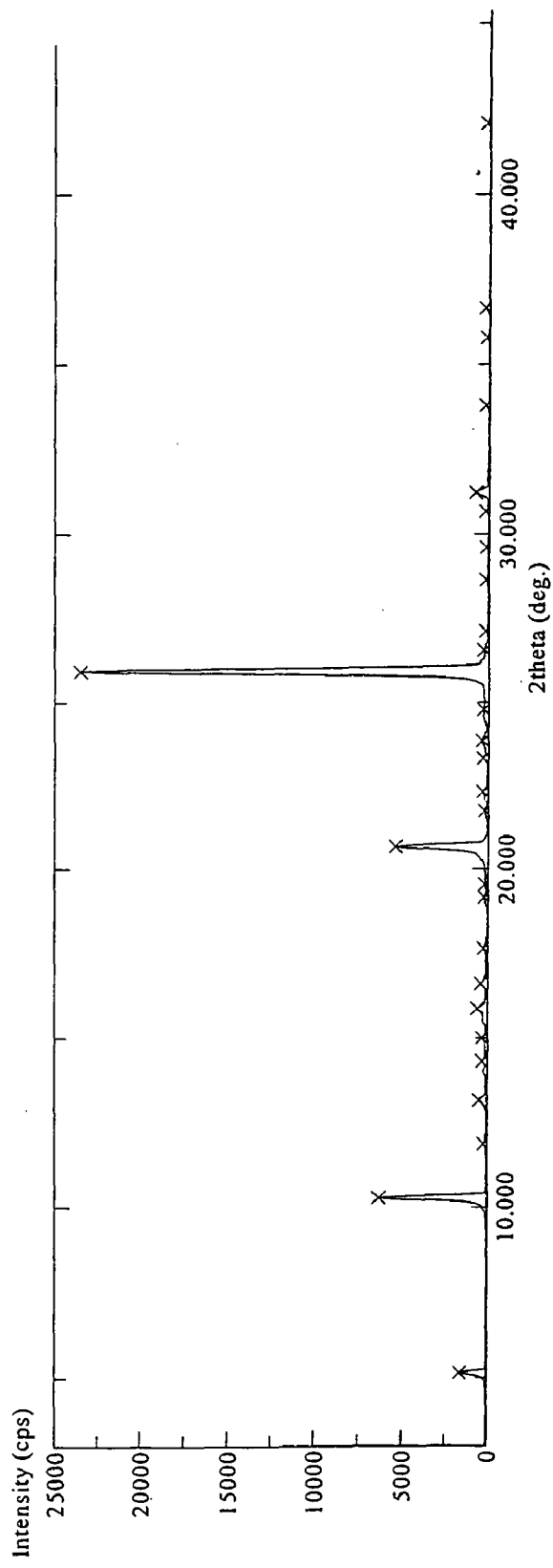

FIG. 3: X-ray powder diffraction (X-RPD) pattern of Form I of desvenlafaxine succinate prepared in Example 2.

Figure 4:
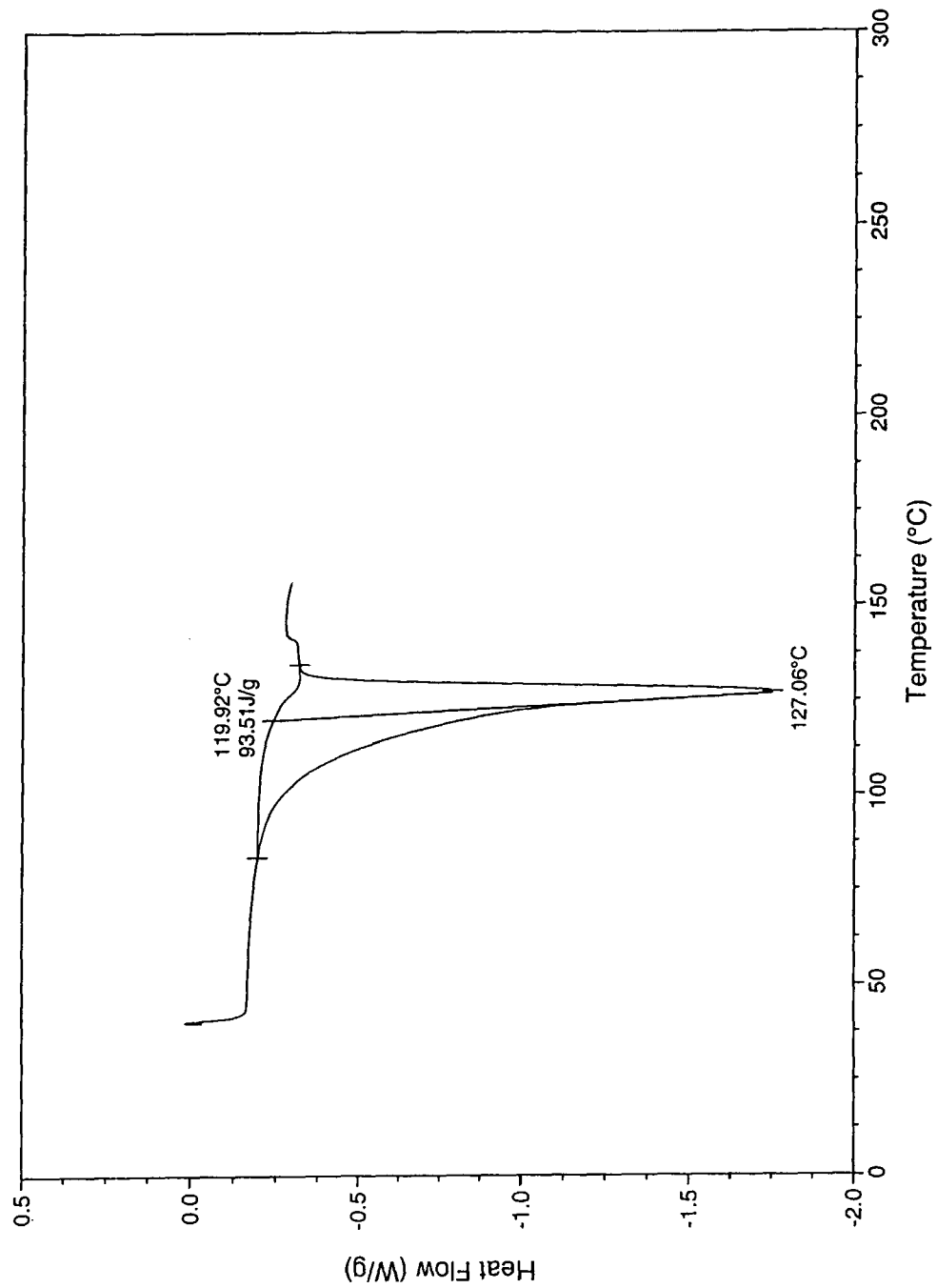

FIG. 4: Differential scanning calorimetry (DSC) of Form I of desvenlafaxine succinate prepared in Example 2.

Figure 5:
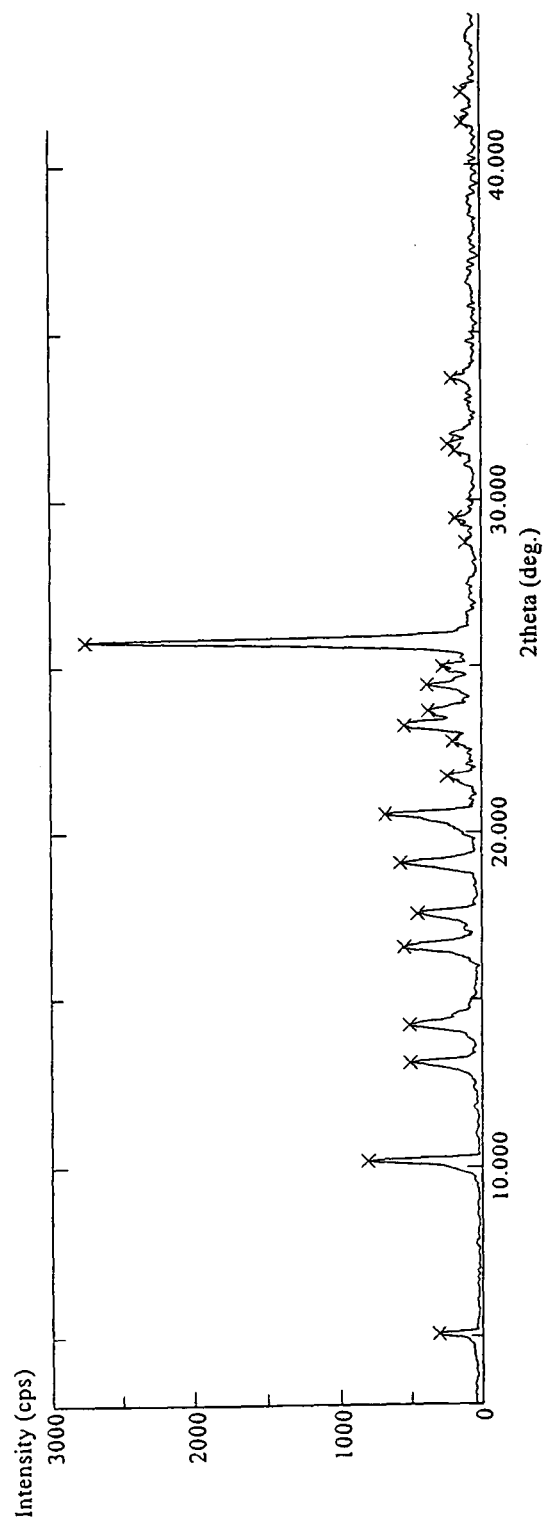

FIG. 5: X-ray powder diffraction (X-RPD) pattern of Form II of desvenlafaxine succinate prepared in Example 3.

Figure 6:
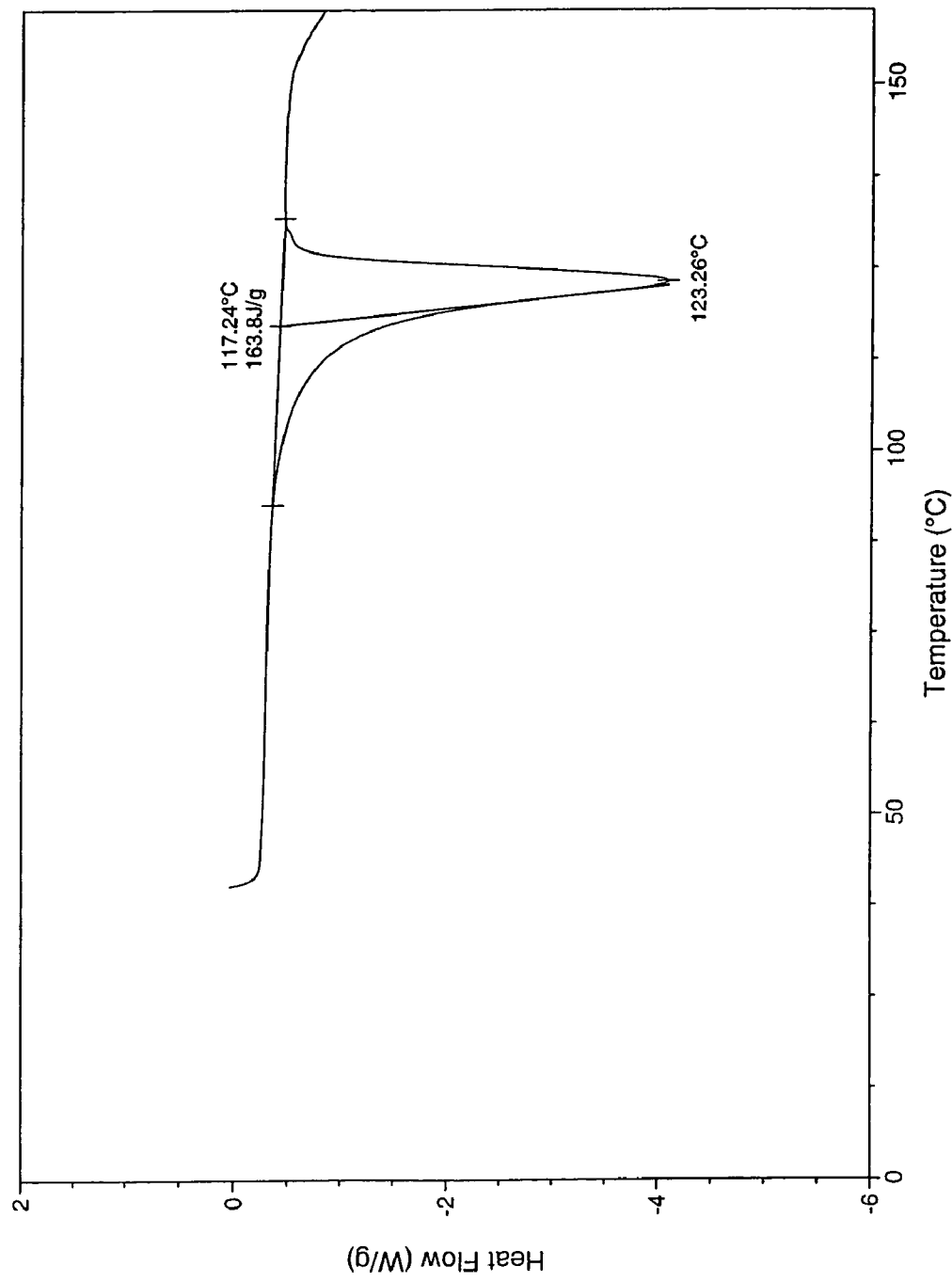

FIG. 6: Differential scanning calorimetry (DSC) of Form II of desvenlafaxine succinate prepared in Example 3

Figure 7:
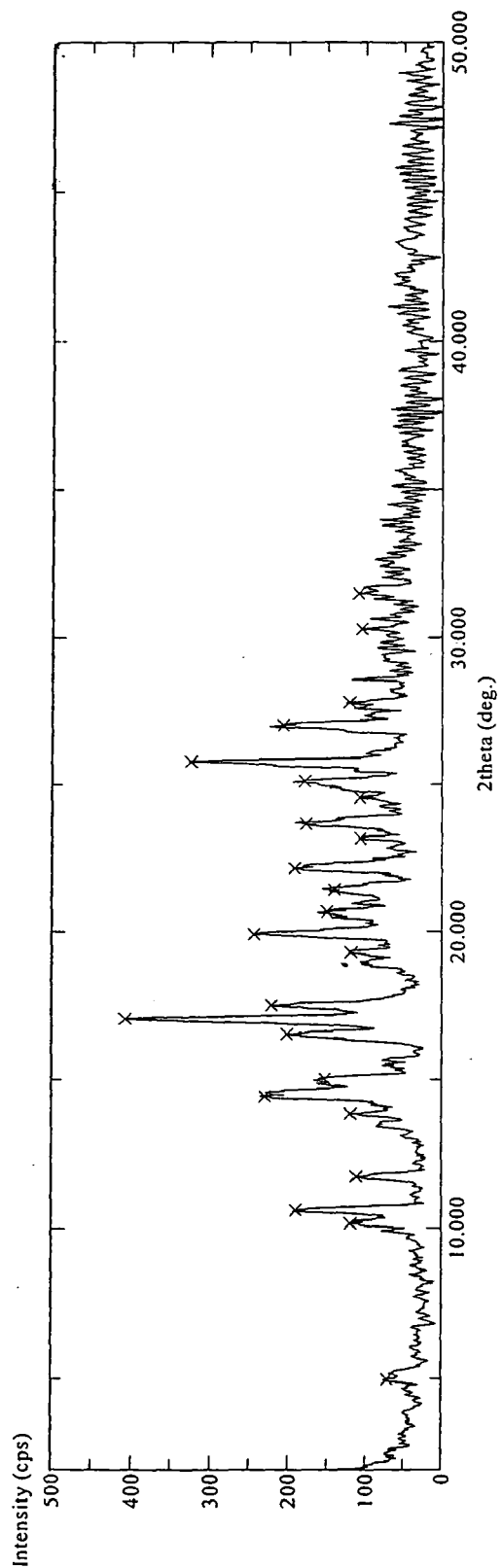

FIG. 7: X-ray powder diffraction (X-RPD) pattern of Form F of desvenlafaxine succinate prepared in Example 5.

Figure 8:
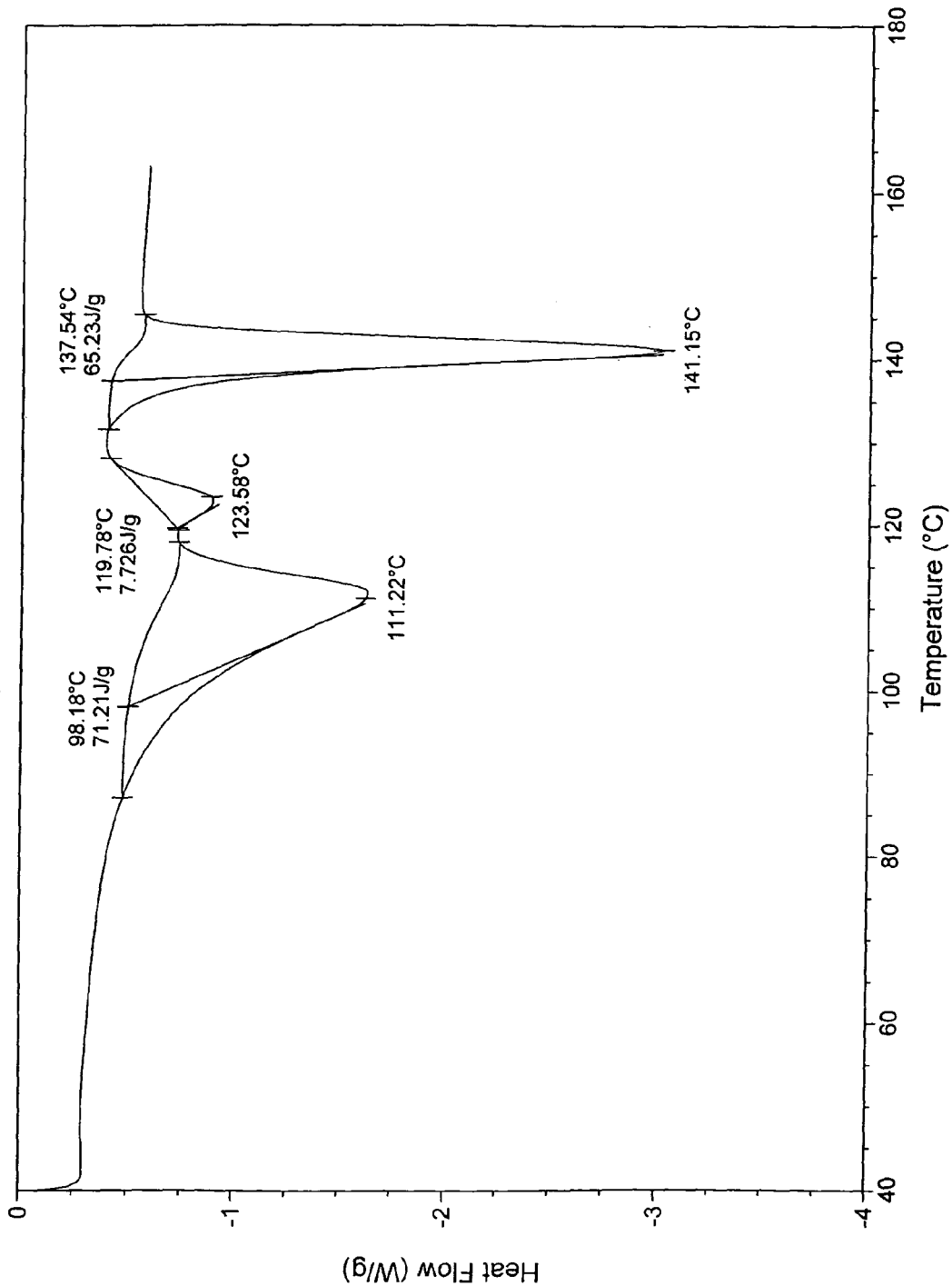

FIG. 8: Differential scanning calorimetry (DSC) of Form F of desvenlafaxine succinate prepared in Example 5.

Figure 9:
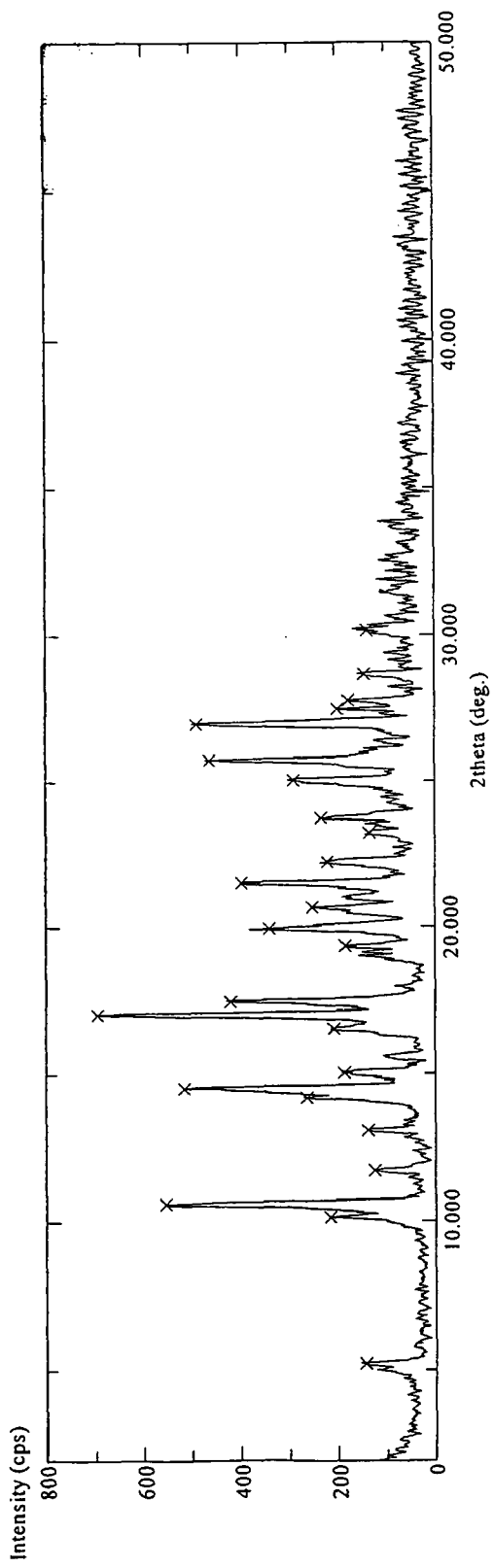

FIG. 9: X-ray powder diffraction (X-RPD) pattern of Form F of desvenlafaxine succinate prepared in Example 7.

Figure 10:
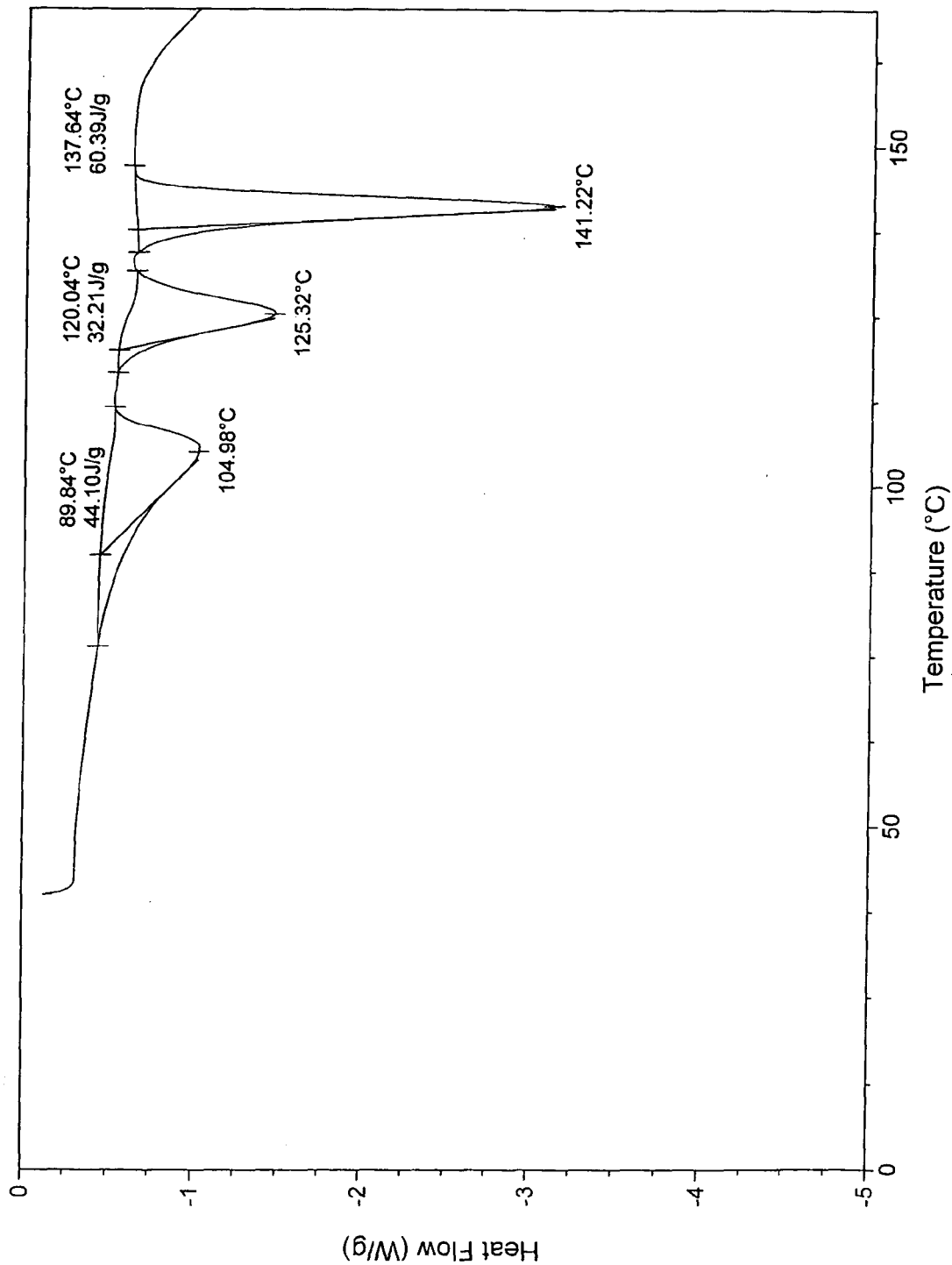

FIG. 10: Differential scanning calorimetry (DSC) of Form F of desvenlafaxine succinate prepared in Example 7.

Figure 11:
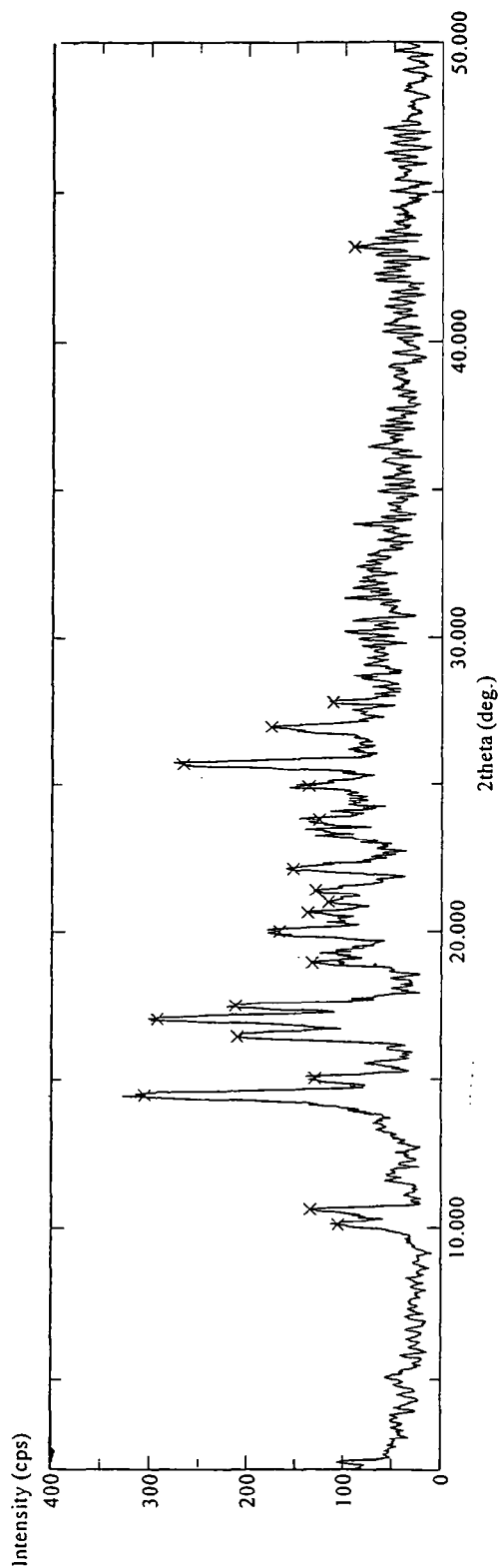

FIG. 11: X-ray powder diffraction (X-RPD) pattern of Form F of desvenlafaxine succinate prepared in Example 8.

DETAILED DESCRIPTION OF THE INVENTION

Unless otherwise indicated, the following definitions are set forth to illustrate and define the meaning and scope of the various terms used to describe the invention herein.

The term "polymorphic form, polymorph, polymorph form or crystalline polymorph of desvenlafaxine succinate" in the present invention refers to a crystal modification of desvenlafaxine succinate, including a crystal modification of desvenlafaxine succinate hydrate, which can be characterized by analytical methods such as X-ray powder diffraction pattern, thermogravimetric analysis (TGA), differential scanning calorimetry (DSC), by its melting point or other techniques.

The term "pharmaceutically acceptable" means that which is useful in preparing a pharmaceutical composition that is generally non-toxic and is not biologically undesirable and includes that which is acceptable for veterinary use and/or human pharmaceutical use.

The term "pharmaceutical composition" or "pharmaceutical formulation" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions of the present invention encompass any composition made by admixing the active ingredient, active ingredient dispersion or composite, additional active ingredient(s), and pharmaceutically acceptable excipients.

The term "composition" is intended to encompass a particular pure polymorphic form or a mixture of a particular polymorphic form along with other polymorph forms, solvate, or amorphous form, hydrate or co-crystals. The composition may comprise a particular polymorphic form from a trace amount or less than 0.1% to 100% (weight by weight) based on the total amount of desvenlafaxine succinate in the composition.

The term "about" generally means within 15%, preferably within 5%, and more preferably within 1% of a given value or range. Alternatively, the term "about" means within an acceptable standard error of the mean, when considered by one of ordinary skill in the art.

According to one aspect of the present invention, there is provided a novel polymorphic form of (1-[2-(dimethylamino)-1-(4-phenol)ethyl]-cyclohexanol succinate (desvenlafaxine succinate), designated as Form V herein, having an X-ray powder diffraction pattern (X-RPD), or substantially the same X-ray powder diffraction pattern, as shown in FIG. 1. More particularly, polymorphic Form V of desvenlafaxine succinate according to the present invention can be characterized as having an X-ray diffraction pattern with characteristic peaks (expressed in 2θ±0.2° 2θ) at one or more of the following positions: 5.08, 10.20, 10.70, 14.58, 17.10, 20.56, 25.80 and 27.12. Form V of desvenlafaxine succinate according to the present invention can be further characterized as having an X-ray diffraction pattern with characteristic peaks (expressed in 2θ±0.2° 2θ) at one or more of the following positions: 5.08, 10.20, 10.70, 13.10, 14.58, 15.12, 16.62, 17.10, 17.58, 19.14, 20.06, 20.56, 21.62, 22.32, 23.26, 23.74, 25.16, 25.80, 27.12, 27.84, 30.38 and 33.72.

Characterizing data for Form V of desvenlafaxine succinate according to the present invention as obtained by X-ray powder diffraction is shown in FIG. 1 and Table 1.

Further characterizing data for Form V of desvenlafaxine succinate according to the present invention as obtained by differential scanning calorimetry (DSC) is shown in FIG. 2, and it provides an endothermic peak at around 115-125° C. (typically about 121° C.) and another endothermic peak at around 136-141° C. (typically 139° C.).

TABLE 1

Characteristic X-ray Powder Diffraction Pattern Peaks (expressed in 2θ ± 0.2° 2θ) and Relative Intensities of Diffraction Lines for Form V of Desvenlafaxine Succinate

| Degree 2θ ± 0.2° 2θ | $I/I_o$ |
| --- | --- |
| 5.08 | 15 |
| 10.20 | 38 |
| 10.70 | 15 |
| 13.10 | 9 |
| 14.58 | 19 |
| 15.12 | 7 |
| 16.62 | 12 |
| 17.10 | 26 |
| 17.58 | 18 |
| 19.14 | 8 |
| 20.06 | 12 |
| 20.56 | 28 |
| 21.62 | 15 |
| 22.32 | 11 |
| 23.26 | 8 |
| 23.74 | 11 |
| 25.16 | 10 |
| 25.80 | 100 |
| 27.12 | 15 |
| 27.84 | 7 |
| 30.80 | 6 |
| 33.72 | 7 |

Further characterizing data for polymorphic Form V of desvenlafaxine succinate according to the present invention was obtained by thermogravimetric analysis (TGA), and it provides a loss of water about 3.0% w/w from 80° C. to 160° C. or a loss of water about 3.5% from 60° C. to 170° C. Therefore, Form V is a crystalline desvenlafaxine succinate hydrate, in which the molar ratio of desvenlafaxine succinate to water is approximately about 3:2. That is, in Form V of desvenlafaxine succinate, about three desvenlafaxine succinate molecules are approximately co-crystallized or associated with two water molecules. The theoretical value of water amount (weight by weight %) in desvenlafaxine succinate monohydrate is 4.7%. Therefore, Form V is between desvenlafaxine succinate monohydrate and desvenlafaxine succinate hemihydrate.

In one favored aspect, the polymorph Form V of desvenlafaxine succinate provides X-ray powder diffraction (X-RPD) pattern substantially in accordance with FIG. 1 and Table 1.

In one favored aspect, the Form V of desvenlafaxine succinate provides differential scanning calorimetry (DSC) substantially in accordance with FIG. 2.

The present invention encompasses Form V of desvenlafaxine succinate isolated in pure form or in a mixture as a solid composition when admixed with other materials, for example the other known polymorphic forms (i.e. amorphous form, solvates, Form I, Form II, Form III, Form IV, Form F, Form G or other forms) of desvenlafaxine succinate or any other materials.

Thus in one aspect there is provided Form V of crystalline desvenlafaxine succinate in isolated solid form.

In a further aspect there is provided Form V of desvenlafaxine succinate in pure form. The pure form means that Form V is over 95% (w/w), preferably over 98% (w/w), more preferably over 99% (w/w %) and most preferably over 99.5% (w/w) or over 99.9% (w/w).

More specifically, the present invention provides that Form V of desvenlafaxine succinate is in the form of a composition or a mixture of Form V along with one or more other crystalline, solvate, amorphous, or other polymorphic forms or their combinations thereof of desvenlafaxine succinate. For example, such a composition may comprise polymorphic Form V along with one or more other polymorphic forms of desvenlafaxine succinate, such as amorphous form, hydrate, solvates, polymorph Form I, Form II, Form III, Form VI, Form F and/or other forms or their combinations thereof. More specifically, the composition may comprise from trace amounts up to 100% Form V, or any amount in between-for example, the composition may comprise less than 0.1%, 0.5%, 1%, 2%, 5%, 10%, 20%, 30%, 40% or 50% by weight of Form V based on the total amount of desvenlafaxine succinate in the composition. Alternatively, the composition may comprise at least 50%, 60%, 70%, 80%, 90%, 95%, 97%, 98%, 99%, 99.5% or 99.9% by weight of Form V based on the total amount of desvenlafaxine succinate in the composition.

In yet a further aspect there is provided Form V of desvenlafaxine succinate in crystalline form.

In a preferred aspect, the particle size of polymorphic Form V of desvenlafaxine succinate in the present invention has the median value of the volume mean diameter of the particles within the range of 0.01 μm-450 μm, preferably 5-250 μm, and most preferably 50-150 μm. Such particles are better in stability, good material flow characteristics, improving the uniformity of dosage forms and thus suitable for bulk preparation and formulation advantages.

According to another aspect, the present invention provides a process for preparing polymorph Form V of desvenlafaxine succinate. Polymorph Form V may be prepared by crystallization from a crystallization solvent containing desvenlafaxine succinate. As used herein, the term "crystallization solvent" means a solvent or combination of solvents from which desvenlafaxine succinate is preferentially crystallized as polymorph Form V. Representative crystallization solvents for preparation of Form V include tetrahydrofruan (THF), methanol, ethanol, propanol, isopropanol, butanol, and combinations thereof. In a preferred aspect, the crystallization solvent comprises THF, to which methanol, ethanol, isopropanol, propanol, butanol or combinations thereof is gradually added.

In a preferred aspect, Form V of desvenlafaxine succinate may be prepared by slurring starting material, crude or pure desvenlafaxine succinate, which can be obtained according to the procedures described in U.S. Pat. Nos. 6,673,838 and 7,026,508 with tetrahydrofuran under heat. The desvenlafaxine succinate is not very soluble in tetrahydrofuran. The polar solvent, for example, the ethanol (e.g., anhydrous ethanol with less than about 0.5% water) or any C1-C4 alcohols or their combinations is then added into the above suspension, and the mixture is heated, suitably to a temperature in the range of from about 45° C. to 85° C., such as about 50° C. to 75° C., for example about 70° C. until all solid materials are dissolved. The clear and hot solution is allowed to cool down to ambient temperature, and the cooled solution is kept at about −5° C.-20° C. for crystallization, preferably at about 2° C.-10° C., and more preferably at about 5° C. The crystal Form V of desvenlafaxine succinate is formed over a period of one to twenty days, and the crystal Form V is recovered from the solvent by filtration. The obtained crystal Form V can be dried under a vacuum oven at about 20° C.-60° C., preferably at about 35° C.-50° C., more preferably at about 35° C.-40° C. for about 6-40 hours to remove the solvent residues.

The concentration of desvenlafaxine succinate within the solution may range from about 0.1% by weight to the saturation point. This concentration will, of course, vary depending upon the temperature at which the co-solvent solution is held, with warmer temperatures generally allowing for the preparation of more concentrated solutions of desvenlafaxine succinate. Preferably, the concentration (w/w %) of desvenlafaxine succinate starting material in solution is about 0.5-15%, preferably about 1-10%, more preferably about 1.5-5%. The volume ratio of tetrahydrofuran to ethanol is about 80:0.1-200, preferably about 80:2-30, more preferably about 100:3-10, most preferably about 100:5-8.

Once obtained, crystals of polymorph Form V may be used as the nucleating agent or "seed" crystals for subsequent crystallizations of polymorph Form V from the crystallization solvent. In one embodiment, the crystallization solvent is formed by dissolving desvenlafaxine succinate in hot THF and ethanol or other suitable crystallization solvents. The crystallization solvent is then seeded with crystals of polymorph Form V, cooled and filtered, resulting in polymorph Form V. In another embodiment, a crystallization solvent is formed by slurring desvenlafaxine succinate in THF and ethanol or other appropriate solvents. The crystallization solvent is then seeded with crystals of polymorph Form V and filtered, resulting in polymorph Form V. Such seeding with crystals of polymorph Form V may take place at any time during the slurring process. Alternatively, seeding with crystals of polymorph Form V may take place prior to, or simultaneously with, addition of desvenlafaxine succinate to the crystallization solvent.

Form V of crystalline desvenlafaxine succinate as obtained above is characterized by X-ray powder diffraction pattern, substantially the same as shown in FIG. 1 and Table 1.

Form V of desvenlafaxine succinate as obtained above is characterized by differential scanning calorimetry (DSC), substantially the same as shown in FIG. 2.

The crystals of desvenlafaxine succinate obtained from recrystallization in solvents as described in above processes may have different crystal habits (e.g., shape), water contents, surface area, bulk or tap density, or particle size, but they are clearly still belonged to a new and novel polymorphic form (Form V) of desvenlafaxine succinate, as they are characterized and confirmed by X-ray powder diffraction pattern and DSC thermogram. The X-ray powder diffraction pattern of Form V is clearly different from that of other known forms such as Form I or Form II, Form III, Form IV as described in U.S. Pat. No. 6,673,838 and Form F as well. In particular, the X-RPD of Form V has a characteristic peak at about 10.7 (expressed in 2θ±0.2° 2θ).

These inventors has reassigned polymorphic "Form VI" of desvenlafaxine succinate disclosed in U. S. provisional patent application No. 60/878,983 as Form I which is described in U.S. Pat. No. 6,673,838. It appears that Form I of desvenlafaxine succinate tends to display some variations in differential scanning calorimetry (DSC) or thermogravimetric analysis (TGA), or even minor changes in its X-RPD relative intensities, particularly when it is obtained under different recrystallization conditions. For example, the grounded Form I crystals (FIG. 1 in U.S. Pat. No. 6,673,838) and ungrounded Form I crystals (FIG. 7 in U.S. Pat. No. 6,673,838) show a slightly different X-RPD profiles. The X-RPD of "Form VI" (FIG. 2 of the present application or U.S. provisional patent application No. 60/878,983) is essentially the same as that of Form I (FIG. 7 in U.S. Pat. No. 6,673,838).

Similarly, these inventors have reassigned the polymorphic "Form VII" desvenlafaxine succinate disclosed in U.S. provisional patent application No. 60/878,983 as Form II which is described in U.S. Pat. No. 6,673,838. It appears that Form II of desvenlafaxine succinate also tends to display some variations in differential scanning calorimetry (DSC) or thermogravimetric analysis (TGA), particularly when it is obtained under different recrystallization conditions. The X-RPD of "Form VII" (FIG. 5 of the present application or U.S. provisional patent application No. 60/878,983) is essentially the same as that of Form II (FIG. 2 in U.S. Pat. No. 6,673,838).

According to another aspect of the present invention, there is provided another novel polymorphic form of (1-[2-(dimethylamino)-1-(4-phenol)ethyl]-cyclohexanol succinate (desvenlafaxine succinate), designated as Form F herein, having an X-ray diffraction pattern, or substantially the same X-ray diffraction pattern, as shown in FIG. 7. More particularly, polymorph Form F of crystalline desvenlafaxine succinate according to the present invention can be characterized as having an X-ray diffraction pattern with characteristic peaks (expressed in 2θ±0.2° 2θ) at one or more of the following positions: 5.22, 10.14, 10.60, 11.70, 14.52, 16.54, 17.04, 17.48, 19.96, 21.52, 25.74 and 26.98. Polymorph Form F of crystalline desvenlafaxine succinate according to the present invention can be further characterized as having an X-ray diffraction pattern with characteristic peaks (expressed in 2θ±0.2° 2θ) at one or more of the following positions: 5.22, 10.14, 10.60, 11.70, 13.06, 14.20, 14.52, 15.04, 16.54, 17.04, 17.48, 19.36 19.96, 20.68, 21.52, 22.20, 23.22, 23.74, 25.04, 25.74, 26.98, 27.48, 27.78, 28.66 and 30.16.

Characterizing data for crystalline polymorph Form F of desvenlafaxine succinate according to the present invention as obtained by X-ray powder diffraction pattern is shown in FIG. 7, FIG. 9 or FIG. 11 and Table 2.

TABLE 2

Characteristic X-ray Powder Diffraction Pattern Peaks (expressed in 2θ ± 0.2° 2θ) and Relative Intensities of Diffraction Lines for Form F of Desvenlafaxine Succinate

| Degree 2θ ± 0.2° 2θ | I/I₀ |
| --- | --- |
| 5.22 | 21 |
| 10.14 | 31 |
| 10.60 | 80 |
| 11.70 | 18 |
| 13.06 | 20 |
| 14.20 | 38 |
| 14.52 | 75 |
| 15.04 | 27 |
| 16.54 | 30 |
| 17.04 | 100 |
| 17.48 | 61 |
| 19.36 | 27 |
| 19.96 | 49 |
| 20.68 | 37 |
| 21.52 | 58 |
| 22.22 | 32 |
| 23.22 | 20 |
| 23.74 | 34 |
| 25.04 | 42 |
| 25.74 | 67 |
| 26.98 | 71 |
| 27.48 | 29 |
| 27.78 | 26 |
| 28.66 | 21 |
| 30.16 | 21 |

Further characterizing data for polymorph Form F of crystalline desvenlafaxine succinate according to the present invention as obtained by differential scanning calorimetry (DSC) is shown in FIG. 8 and FIG. 10, and it provides three characteristic endothermic peaks at around 100-115° C., around 121-127° C. and around 138-143° C., respectively. In particular, the polymorph Form F exhibits a characteristic and predominant peak at about 138-143° C. in DSC.

Further characterizing data for polymorph Form F of crystalline desvenlafaxine succinate according to the present invention as obtained by thermogravimetric analysis (TGA), and it provides a loss of water at about 1.4% to 2.8% w/w from about 60° C. to 125° C. Therefore, Form F is a crystalline desvenlafaxine succinate hemihydrate, in which the molar ratio of desvenlafaxine succinate to water is about 2:1. That is, in Form F of desvenlafaxine succinate, about two desvenlafaxine succinate molecules are co-crystallized or associated with one water molecule. Form F displays a characteristic profile of TGA by losing most of water at around 80° C.-110° C. in TGA. However, other forms such as Form I, Form II, Form III, Form VI and Form V do not lose most of their water at around 80° C.-160° C. in TGA. The current inventors have surprisingly discovered a new and novel crystalline form (Form F) of desvenlafaxine succinate, which displays an unusual DSC and TGA profiles, low water contents (e.g., within hemihydrate range), better thermal stability and material flow character, and an unique X-RPD spectrum.

It is known that desvenlafaxine succinate tends to form monohydrate or a hydrate between hemihydrate and monohydrate, as shown in U.S. Pat. No. 6,673,838. These inventors have discovered that even under nitrogen atmosphere in dried solvents (ethyl acetate and isopropyl alcohol is dried with magnesium sulphate), recrystallization of desvenlafaxine succinate still forms a monohydrate (e.g., Form II) as shown in Example 4. The anhydrous desvenlafaxine succinate (Form IV) can be only obtained from heating a solid composition of Form I and Form II for eighteen hours 120° C., as disclosed in Example 10 of U.S. Pat. No. 6,673,838.

Among all polymorphic hydrate forms of desvenlafaxine succinate discovered so far, Form F has the highest melting point as determined by DSC (at about 138-143° C.) and lowest water contents as determined by TGA. Therefore, Form F is more thermodynamically stable than other known hydrate forms other than anhydrous Form IV. These characteristics render Form F is superior to other known Forms of desvenlafaxine succinate in terms of thermal stability and physical stability. Additionally, the shape of Form F crystals is round particles with a very good flow character. Other forms of desvenlafaxine succinate, such as Form I, usually form crystals with a needle-like shape, which is unfavorable to the development of pharmaceutical formulations.

Form F crystals obtained from recrystallization under different solvent systems display some variations in its DSC and TGA, even some minor variations in the X-RPD spectrum or data. As shown in Table 3, the relative peak height ratio of the peak at about 100-115° C. to the peak at about 138-143° C. in DSC is proportional to the water content present in the sample as determined by TGA.

More specifically, the present invention provides that Form F is in the form of a composition or a mixture of polymorph Form F along with one or more polymorphic forms, hydrate, solvate, amorphous, or other crystalline forms or combinations thereof of desvenlafaxine succinate. For example, such a composition may comprise polymorph Form F along with one or more other polymorphic forms of desvenlafaxine succinate, such as amorphous form, hydrate, solvates, polymorph Form I, Form II, Form III, Form VI, Form V and/or other forms or their combinations thereof. More specifically, the composition may comprise from trace amounts up to 100% Form F, or any amount in between-for example, the composition may comprise less than 0.1%, 0.5%, 1%, 2%, 5%, 10%, 20%, 30%, 40% or 50% by weight of polymorph Form F based on the total amount of desvenlafaxine succinate in the composition. Alternatively, the composition may comprise at least 50%, 60%, 70%, 80%, 90%, 95%, 97%, 98%, 99%, 99.5% or 99.9% by weight of polymorph Form F based on the total amount of desvenlafaxine succinate in the composition.

TABLE 3

Comparison of Form F Obtained From Three Solvent Systems

| Recrystallization solvents | DSC endothermic peaks | Approximately peak height ratio of the peak at 100-115° C. to the peak at 138-143° C. | Amount of water loss at 60-110° C. in TGA | Amount of water loss at 80-120° C. in TGA |
|---|---|---|---|---|
| Cyclohexane/ IPA* | 110.42° C. (broad peak), 122.19° C. and 139.63° C. (predominant and sharp peak) | 50% | 2.8% | 2.4% |
| DCM*/ cyclohexane/ acetonitrile/ ethanol | 111.22° C. (broad peak), 123.58° C. and 141.15° C. (predominant and sharp peak) | 25% | 1.8% | 1.4% |
| Cyclohexane/ THF/IPA* | 104.98° C. (broad peak), 125.98° C. and 141.22° C. (predominant and sharp peak) | 40% | 2.5% | 2.4% |

*Note:
IPA is isopropyl alcohol; DCM is dichloromethane; THF is tetrahydrofuran.

In one favored aspect, the polymorph Form F provides X-ray powder diffraction (X-RPD) pattern substantially in accordance with FIG. 7, FIG. 9, FIG. 11 or Table 2.

In one favored aspect, the polymorph Form F provides differential scanning calorimetry (DSC) substantially in accordance with FIG. 8 or FIG. 10.

The present invention encompasses Form F of desvenlafaxine succinate isolated in pure form or in a mixture as a solid composition when admixed with other materials, for example the known forms (i.e. amorphous form, Form I, Form II, Form III, Form IV, Form V or other forms) of desvenlafaxine succinate or any other materials.

Thus in one aspect there is provided Form F of desvenlafaxine succinate in isolated solid form.

In a further aspect there is provided Form F of desvenlafaxine succinate in pure form. The pure form means that polymorph Form F is over 95% (w/w), preferably over 98% (w/w), more preferably over 99% (w/w) and most preferably over 99.5% (w/w) or over 99.9% (w/w).

In yet a further aspect there is provided polymorph Form F of desvenlafaxine succinate in crystalline form.

In a preferable aspect, the particle size of Form F of desvenlafaxine succinate in the present invention has the median value of the volume mean diameter of the particles within the range of about 0.01 μm-450 μm, preferably about 5-250 μm, and most preferably about 50-150 μm. Such particles are better in stability, have good material flow characteristics and thus suitable for bulk preparation and formulation advantages.

In a further aspect, the present invention provides a process for preparing Form F of desvenlafaxine succinate. Polymorph Form F may be prepared by crystallization from a crystallization solvent containing desvenlafaxine succinate. As used herein, the term "crystallization solvent" means a solvent or combination of solvents from which desvenlafaxine succinate is preferentially crystallized as polymorph Form F. Representative crystallization solvents include polar solvents, non-polar solvents, protic solvents and aprotic solvents, and more specifically include methylene chloride, methanol, ethanol, propanol, isopropanol, butanol, ethyl acetate, tetrahydrofruan (THF), diethyl ether, methyl t-butyl ether, acetonitrile, and combinations thereof. In one preferred embodiment, the crystallization solvent comprises cyclohexane, to which isopropanol, ethanol, acetonitrile or combinations thereof is gradually added.

Once obtained, crystals of polymorph Form F may be used as the nucleating agent or "seed" crystals for subsequent crystallizations of polymorph Form F from the crystallization solvent. In one embodiment, the crystallization solvent is formed by dissolving desvenlafaxine succinate in hot cyclohexane, THF, isopropyl alcohol, ethanol or other suitable crystallization solvents. The crystallization solvent is then seeded with crystals of polymorph Form F, cooled and filtered, resulting in polymorph Form F. In another embodiment, a crystallization solvent is formed by slurring desvenlafaxine succinate in cyclohexane, THF, isopropyl alcohol, ethanol or other appropriate solvents. The crystallization solvent is then seeded with crystals of polymorph Form F and filtered, resulting in polymorph Form V. Such seeding with crystals of polymorph Form F may take place at any time during the slurring process. Alternatively, seeding with crystals of polymorph Form F may take place prior to, or simultaneously with, addition of desvenlafaxine succinate to the crystallization solvent.

The concentration of desvenlafaxine succinate within the solution may range from 0.1% by weight to the saturation point. This concentration will, of course, vary depending upon the temperature at which the solution is held, with warmer temperatures generally allowing for the preparation of more concentrated solutions of desvenlafaxine succinate. Preferably, the concentration (w/w %) of desvenlafaxine succinate starting material in solution is about 0.5-15%, preferably about 1-10%, more preferably about 1.5-5%.

In a preferred aspect, Form F of desvenlafaxine succinate may be prepared by slurring starting material, crude or pure desvenlafaxine succinate, which can be obtained according to the procedures described in U.S. Pat. Nos. 6,673,838 and 7,026,508 with a mixture of cyclohexane and a polar or a non-polar organic solvent or their mixtures under heat, or a mixture of 1,2-dichloroethane and a polar organic solvent under heat.

The preferred polar organic solvents are selected from a group consisting of acetonitrile, tetrahydrofuran (THF), methanol, ethanol, isopropyl alcohol, n-butyl alcohol, any C1-C4 alcohol solvents. The more preferred polar organic solvents are selected from a group consisting of acetonitrile, tetrahydrofuran (THF), methanol, ethanol, propanol and isopropyl alcohol. The most preferred polar organic solvents are selected from a group consisting of acetonitrile, tetrahydrofuran (THF), ethanol, propanol or isopropyl alcohol. The preferred non-polar organic solvents are selected from a group consisting of dichloromethane, ethyl acetate or any ethers. The more preferred non-polar organic solvents are selected from a group consisting of dichloromethane or ethyl acetate. The most preferred non-polar organic solvent is dichloromethane.

The volume ratio of cyclohexane to polar solvent or non-polar solvent or their mixtures is about 1:0.1-10, preferably about 1:0.2-5, more preferably about 1:0.4-2, most preferably about 1:0.5-1.5.

In a preferred aspect, the recrystallization solvents for preparation of Form F are a mixture of cyclohexane, tetrahydrofuran and isopropyl alcohol with a volume ratio of preferably about 1-p4:1-4:0.1-2, more preferably about 2-3:2-3: 0.3-1, most preferably about 2.5:2.5:0.5.

In another preferred aspect, the recrystallization solvents for preparation of Form F are a mixture of cyclohexane, acetonitrile, dichloromethane and ethanol with a volume ratio of about 1-4:1-3:0.1-2, more preferably about 2-3:1.5-2.5: 0.3-1, most preferably about 2:1.5:2:0.5.

In a still preferred aspect, the recrystallization solvents for preparation of Form F are a mixture of cyclohexane and isopropyl alcohol with a volume ratio of about 2-6:1-4, more preferably about 3-5:2-4, most preferably about 4:3.

In a further preferred aspect, the recrystallization solvents for preparation of Form F are a mixture of 1,2-dichloroethane and acetonitrile with a volume ratio of about 0.5-5:0.2-3, more preferably about 1.5-3.5:0.5-1.5, most preferably about 2:1.

In a still preferred aspect, the solvent mixtures for preparation of Form F are in a homogeneous solution, and solvents are mixable.

The suspension mixture is heated, suitably to a temperature in the range of from about 35° C. to 85° C., such as about 45° C. to 75° C., for example about 50-70° C. until all solid materials are dissolved. The hot solution is allowed to cool down to ambient temperature, and the cooled solution is kept at about −18° C.-30° C. for crystallization, preferably at about −5-25° C., and more preferably at about 0-15° C., and most preferably at about 5° C. The Form F of desvenlafaxine succinate is formed over a period of one to five days upon the growth of crystals. The Form F is recovered from the solvent, typically by filtration to remove the solvents. The obtained Form F can be dried under a vacuum oven at about 20-60° C., preferably at about 35-50° C., more preferably at about 38-43° C. for about 24-48 hours to remove the solvent residues. The concentration (w/w %) of desvenlafaxine succinate in solution for recrystallization is about 0.5-25%, preferably 1-about 20%, more preferably about 1.5-10%.

Optionally, the solution mixture is seeded with Form F of desvenlafaxine succinate.

Form F of desvenlafaxine succinate as obtained above is characterized by X-ray powder diffraction pattern, substantially the same as shown in FIG. 7, FIG. 9, FIG. 11 or Table 2.

Form F of desvenlafaxine succinate as obtained above is characterized by differential scanning calorimetry (DSC), substantially the same as shown in FIG. 8 or FIG. 10.

The crystals of desvenlafaxine succinate obtained from recrystallization in various solvents as described in above processes may have different crystal habits (e.g., shape), water contents, surface area, bulk or tap density, or particle size, may contain a certain amount of other forms such as amorphous form, Form I, Form II, Form III, Form VI or Form V, but the main component in the solid composition is clearly still belonged to a new and undisclosed polymorphic form (Form F) of desvenlafaxine succinate, as they are characterized and confirmed by X-ray powder diffraction pattern and DSC thermogram.

According to a further aspect, the present invention further provides a pharmaceutical composition, which comprises a therapeutically effective amount of polymorph Form V or Form F of desvenlafaxine succinate, substantially as hereinbefore described, together with one or more pharmaceutically acceptable carriers, diluents or excipients, additives, fillers, lubricants, solvents, binders or stabilizers, optionally, one or more other active ingredients.

Pharmaceutical compositions as provided by the present invention can be prepared by known procedures using well-known and readily available ingredients. In preparation of compositions as provided by the present invention, polymorph Form V, or Form F of crystalline desvenlafaxine succinate, substantially as hereinbefore described, can be mixed with one or more carriers, excipients, diluents, additives, fillers, lubricants, solvents, binders or stabilizers, optionally, one or more other active ingredients.

Pharmaceutical compositions as provided by the present invention can be in the form of tablets, pills, powders, lozenges, sachets, cachets, elixirs, suspensions, emulsions, solutions, syrups, aerosol, ointments soft and hard gelatin capsules, suppositories, sterile injectable solutions and sterile packaged powders containing, for example, up to 70% by weight of polymorph Form V or Form F, substantially as hereinbefore described.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl- and propylhydroxybenzoates, talc, magnesium stearate and mineral oil. The compositions can additionally include lubricating agents, wetting agents, and emulsifying and suspending agents, preserving agents, sweetening agents or flavoring agents.

According to a still another embodiment, the pharmaceutical composition comprises an effective dosage amount of desvenlafaxine succinate, wherein desvenlafaxine succinate comprises at least a certain percentage of polymorph Form V (based on the total amount of desvenlafaxine succinate present in the composition—that is, the total amount of desvenlafaxine succinate being 100%). In other words, at least a certain percentage of desvenlafaxine succinate present within the pharmaceutical composition exists as polymorph Form V, with the remainder of desvenlafaxine succinate being in a different form, including (but not limited to) polymorph Form I, Form II, Form III, Form VI, Form F or any other crystalline, solvate or amorphous form(s).

According to a still further embodiment, the pharmaceutical composition comprises an effective dosage amount of desvenlafaxine succinate, wherein desvenlafaxine succinate comprises at least a certain percentage of polymorph Form F (based on the total amount of desvenlafaxine succinate present in the composition—that is, the total amount of desvenlafaxine succinate being 100%). In other words, at least a certain percentage of desvenlafaxine succinate present within the pharmaceutical composition exists as polymorph Form F, with the remainder of desvenlafaxine succinate being in a different form, including (but not limited to) polymorph Form I, Form II, Form III, Form VI, Form V or any other crystalline, solvate or amorphous form(s).

The pharmaceutical compositions of the invention may be formulated so as to provide quick, extended, sustained or delayed release of polymorph Form V or Form F of desvenlafaxine succinate, substantially as hereinbefore described, after administration to the patient by employing procedures well known in the art. The pharmaceutical compositions of the invention may be preferably formulated so as to provide delayed, extended or sustained release tablets consisting of polymorph Form V or Form F of desvenlafaxine succinate, substantially as hereinbefore described as active ingredient and plus any additional excipients suitable for preparation of delayed, extended or sustained release tablets.

According to one preferred aspect, the pharmaceutical composition is an extended release formulation. For example, an extended release formulation may comprise spheroids comprised of crystalline polymorph Form V or Form F of desvenlafaxine succinate, microcrystalline cellulose, and, optionally, hydroxypropylmethylcellulose. The spheroids are preferably coated with a film coating composition comprised of ethyl cellulose and hydroxypropylmethylcellulose.

According to another preferred embodiment, the pharmaceutical composition is a sustained release formulation (e.g., in the form of a tablet). The sustained release formulation may comprise crystalline polymorph Form V or Form F of desvenlafaxine succinate, a release rate controlling excipient, and optionally other adjuvants. Suitable rate controlling excipients include, but are not limited to, hydroxyalkyl cellulose, such as hydroxypropyl cellulose and hydroxypropyl methyl cellulose (HPMC); poly(ethylene) oxide; alkyl cellulose, such as ethyl cellulose and methyl cellulose; carboxymethyl cellulose; hydrophilic cellulose derivatives; carboxyvinylpolymers (e.g., Carbopol 971P), polyvinylpyrrolidone (PVP) derivatives and polyethylene glycol derivatives.

The sustained release pharmaceutical composition comprises about 10-600 mg of polymorphs Form V or Form F of desvenlafaxine succinate and about 15 w/w to about 70% w/w of a release rate controlling pharmaceutical excipients. A preferred sustained release pharmaceutical composition comprises from about 100-400 mg of crystalline. polymorphs Form V or Form F of desvenlafaxine succinate and about 10 w/w to about 66% w/w of hydroxypropyl methylcellulose, methyl cellulose or ethyl cellulose. Typically, the sustained release formulation provides sustained therapeutically effective plasma levels over at least about 12 or 24 hour period. The peak serum levels during the 12 or 24 hour period are generally up to 150 ng/ml.

The pharmaceutical compositions are preferably formulated in a unit dosage form, each dosage containing from about 2 to about 500 mg, more usually about 20 to about 300 mg, of polymorph Form V or Form F of desvenlafaxine succinate, substantially as hereinbefore described. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

A further aspect of the present invention relates to a method of treating or preventing patients suffering from depression (e.g., major depressive disorder, bipolar disorder, and dysthymia), anxiety, panic disorder, generalized anxiety disorder, post traumatic stress disorder, premenstrual dysphoric disorder, fibromyalgia, agoraphobia, attention deficit disorder, obsessive compulsive disorder (including trichotillomania), social anxiety disorder, schizophrenia, obesity, anorexia nervosa, vasomotor flushing, cocaine and alcohol addiction, borderline personality disorder, cognitive enhancement, cognitive impairment, and cessation of smoking or other tobacco uses and certain complications thereof, comprising administering to a patient in need of such treatment an effective amount of a pharmaceutical composition comprising polymorph Form V or Form F of desvenlafaxine succinate and a pharmaceutically acceptable carrier.

The present invention further provides polymorph Form V or Form F of desvenlafaxine succinate, for use in the manufacture of a medicament for the treatment and/or prophylaxis of patients suffering from depression (e.g., major depressive disorder, bipolar disorder, and dysthymia), anxiety, panic disorder, generalized anxiety disorder, post traumatic stress disorder, premenstrual dysphoric disorder, fibromyalgia, agoraphobia, attention deficit disorder, obsessive compulsive disorder (including trichotillomania), social anxiety disorder, schizophrenia, obesity, anorexia nervosa, vasomotor flushing, cocaine and alcohol addiction, borderline personality disorder, cognitive enhancement, cognitive impairment, and cessation of smoking or other tobacco uses and certain complications thereof.

The particular dose of polymorph Form V or Form F of desvenlafaxine succinate, substantially as hereinbefore described, administered according to this invention will of course be determined by the particular circumstances surrounding the case, the route of administration, the particular condition being treated, and similar considerations.

Polymorph Form V or Form F of desvenlafaxine succinate, substantially as hereinbefore described, can be administered by a variety of routes including the oral, rectal, transdermal, subcutaneous, intravenous, intramuscular or intranasal routes. A typical daily dose will contain from about 0.1 mg/kg to about 50 mg/kg of polymorph Form V or Form F of the present invention. Preferred daily doses will be about 0.5 to about 15 mg/kg, ideally about 1 to about 2 mg/kg.

Having thus described the invention with reference to particular preferred embodiments, those in the art can appreciate modifications to the invention as described and illustrated that do not depart from the spirit and scope of the invention as disclosed in the specification. The following examples are set to illustrate the invention, and aid to understanding the invention, but not intended to, and should not be construed to limit its scope in any way.

EXPERIMENTAL

Thermogravimetric analysis (TGA) measurements were performed in a Pyris I TGA of Perkin-Elmer (TGA7) under nitrogen purge. The sample was heated from 40° C. to 220° C. at a scan rate of 10° C./minute.

DSC measurements were performed in a TA instrument with a sealed pan at a scan rate of 10° C./minute from 40° C. to 280° C. under nitrogen purge.

X-ray powder diffraction (X-RPD) data were obtained by ARL X-Ray powder diffractometer model XTRA-030. Scanning range 3-50 deg. 2 theta, continuous scan, rate 3 deg./min. The accuracy of peak positions was defined as +/−0.2 degrees due to such experimental differences as instrumentation and sample preparation etc.

EXAMPLES

Example 1

Preparation of Polymorph Form V of Desvenlafaxine Succinate

Desvenlafaxine succinate (2.0 g) was suspended in about 80 ml boiling tetrahydrofuran (HPLC grade). To the suspension was added about 5 ml ethanol (reagent grade, anhydrous) until all solid materials are dissolved. The resulting solution was then cooled down to ambient temperature, and some crystals were formed after six days. The recrystallization was continued at about 5° C. for five days. The resulting crystal was isolated by filtration and dried in vacuum oven at about 35° C. for overnight and then at about 40° C. for about 5 hours to give a white crystalline solid (about 1.5 g). DSC, TGA and X-ray diffraction pattern techniques were used to characterize the obtained product. DSC experiment of the obtained product showed an endothermic peak at about 121.32° C. and another endothermic peak at about 139.18° C., as shown in FIG. 2. Powder X-ray diffraction pattern of the obtained product is shown in FIG. 1. The TGA showed that the obtained product contains about 3.0% water.

Example 2

Preparation of Polymorph Form I of Desvenlafaxine Succinate Desvenlafaxine succinate (3.5 g) was suspended in 80 ml boiling methanol (HPLC grade) and 13 ml dichloromethane (HPLC grade). The suspension was heated up until all solid materials were dissolved and the mixture became a homogeneous solution. The resulting solution was cooled down to ambient temperature, and then kept at ambient temperature under fume hood for five days. The resulting crystal was isolated by filtration and dried in vacuum oven at about 35° C. for overnight and then at about 40° C. for about 5 hours to give a white crystalline solid (about 2.2 g). DSC, TGA and X-ray diffraction pattern techniques were used to characterize the obtained product. DSC experiment of the obtained product showed an endothermic peak at about 127.06° C., as shown in FIG. 4. Powder X-ray diffraction pattern of the obtained product is shown in FIG. 3. The TGA showed that the obtained product contains about 3.2% water.

Example 3

Preparation of Polymorph Form II of Desvenlafaxine Succinate

Desvenlafaxine succinate (2.0 g) was suspended in 80 ml boiling isopropanol (HPLC grade). The suspension was heated up until all solid materials were dissolved and the mixture became a clear and homogeneous solution. The resulting solution was cooled down to ambient temperature, and then kept at about 5° C. for overnight, and some crystal was formed next morning. The recrystallization was continued at about 5° C. for five days. The resulting crystal was isolated by filtration and dried in vacuum oven at about 35° C. for overnight and then at about 40° C. for about 5 hours to give a white crystalline solid (about 1.2 g). DSC, TGA and X-ray diffraction pattern techniques were used to characterize the obtained product. DSC experiment of the obtained product showed an endothermic peak at about 123.26° C., as shown in FIG. 6. Powder X-ray diffraction pattern of the obtained product is shown in FIG. 5. The TGA showed the obtained product contains about 4.2% water.

Example 4

Preparation of Polymorph Form II of Desvenlafaxine Succinate

Desvenlafaxine succinate (2.5 g) was suspended in about 20 ml boiling ethyl acetate and about 20 mL isopropanol (HPLC grade). The suspension was heated up until all solid materials were dissolved and the mixture became a clear and homogeneous solution. To the clear solution was added about 3.0 g anhydrous magnesium sulphate (reagent grade). The suspension was allowed to cool down for a few minutes, and clear portion of the solution was transferred into another clear flask to remove magnesium sulphate residue. The solution was then saturated with nitrogen gas and sealed tightly by parafilm. The resulting solution was cooled down to ambient temperature, and then kept at about 5° C. for overnight, and some crystal was formed next morning. The recrystallization was continued at 5° C. for additional two more days. The resulting crystal was isolated by filtration and dried in vacuum oven at about 40° C. for about 30 hours to give a white crystalline solid (about 1.2 g). DSC, TGA and X-ray diffraction pattern techniques were used to characterize the obtained product. DSC experiment of the obtained product showed an endothermic peak at about 122.13° C., substantially same as shown in FIG. 6. Powder X-ray diffraction pattern of the obtained product is substantially same as shown in FIG. 5. The TGA showed the obtained product contains about 4.5% water.

Example 5

Preparation of Polymorph Form F of Desvenlafaxine Succinate

Desvenlafaxine succinate (about 2.5 g) was suspended in about 25 ml hot or boiling cyclohexane (HPLC grade), about 25 mL tetrahydrofuran (HPLC grade) and about 5 mL isopropanol (HPLC grade). The suspension was heated up until all solid materials were dissolved and the mixture became a clear and homogeneous solution. The resulting solution was cooled down to ambient temperature, and then kept at about 5° C. for over weekend, and crystals were formed after two days. The resulting crystals were isolated by filtration and dried in vacuum oven at about 40° C. for about 30 hours to give a white crystalline solid (about 1.5 g). DSC, TGA and X-ray diffraction pattern techniques were used to characterize the obtained product. DSC experiment of the obtained product showed an endothermic peak at about 111.22° C., at about 123.58° C. and at about 141.15° C., as shown in FIG. 8. Powder X-ray diffraction pattern of the obtained product is shown in FIG. 7. The TGA showed the obtained product contains about 2.5% water.

Example 6

Preparation of Polymorph Form F of Desvenlafaxine Succinate

Desvenlafaxine succinate (about 2.5 g) was suspended in about 40 ml hot or boiling cyclohexane (HPLC grade) and about 30 mL isopropanol (HPLC grade). The suspension was heated up until all solid materials were dissolved and the mixture became a clear and homogeneous solution. The resulting solution was cooled down to ambient temperature, and then kept at about 5° C. for overnight, and crystals were formed next morning. The resulting crystals were isolated by filtration and dried in vacuum oven at about 40° C. for about 30 hours to give a white crystalline solid (about 1.6 g). DSC, TGA and X-ray diffraction pattern techniques were used to characterize the obtained product. DSC experiment of the obtained product showed an endothermic peak at about 110.42° C. (broad peak), at about 122.19° C. and at about 139.63° C. Powder X-ray diffraction pattern of the obtained product is essentially same as shown in FIG. 7. The TGA showed the obtained product contains about 2.4% water.

Example 7

Preparation of Polymorph Form F of Desvenlafaxine Succinate

Desvenlafaxine succinate (about 2.5 g) was suspended in about 20 ml hot or boiling cyclohexane (HPLC grade) and about 20 dichloromethane (HPLC grade), about 15 mL acetonitrile (HPLC grade) and about 5 mL ethanol (HPLC grade, anhydrous). The suspension was heated up until all solid materials were dissolved and the mixture became a clear and homogeneous solution. The resulting solution was cooled down to ambient temperature, and then kept at about 5° C. for overnight, and crystals were formed next morning. The resulting crystals were isolated by filtration, washed by cold methyl t-butyl ether (about 2×10 mL) and dried in vacuum oven at about 40° C. for about 30 hours to give a white crystalline solid (about 1.2 g). DSC, TGA and X-ray diffraction pattern techniques were used to characterize the obtained product. DSC experiment of the obtained product showed an endothermic peak at about 104.98° C. (broad peak), at about 125.32° C. and about 141.22° C., as shown in FIG. 10. Powder X-ray diffraction pattern of the obtained product is shown in FIG. 9. The TGA showed the obtained product contains about 1.4% water.

Example 8

Preparation of Polymorph Form F of Desvenlafaxine Succinate

Desvenlafaxine succinate (about 2.0 g) was suspended in about 20 ml hot or boiling 1,2-dichloroethane (HPLC grade) and about 10 mL acetonitrile (HPLC grade). The suspension was heated up until all solid materials were dissolved and the mixture became a clear and homogeneous solution. The resulting solution was cooled down to ambient temperature, and then kept at about 5° C. for over weekend, and crystals were formed after two days. The resulting crystals were isolated by filtration and dried in vacuum oven at about 40° C. for about 30 hours to give a white crystalline solid (about 1.0 g). DSC, TGA and X-ray diffraction pattern techniques were used to characterize the obtained product. DSC experiment of the obtained product showed an endothermic peak at about 114.70° C. (broad peak) and at about 138.37° C. Powder X-ray diffraction pattern of the obtained product is shown in FIG. 11. The TGA showed the obtained product contains about 3.0% water.

Example 9

Formulation of Tablets Containing Crystalline Form V or Form F of Desvenlafaxine Succinate There were three major steps involved in manufacturing the tablets: (A) preparation of polymorph forms (any forms of Form V or Form F) of desvenlafaxine succinate granular concentrate; (B) preparation of tablet core; (C) coating the tablet core. The amount of each ingredient included in the formulation is shown in Table 6 (quantity in gram).

A: Preparation of Polymorph Form V or Form F of Desvenlafaxine Succinate Granular Concentrate The following ingredients (quantity in gram) were sifted through a clean screen (typically 0.066"): lactose anhydrous, pregelatinized starch, sodium starch glycolate and microcrystalline cellulose.

The screened materials were transferred into a high shear (high-energy) mixer and blended for ten (10) minutes at 100 rpm. The blended material was granulated with purified water. The wet granules were passed through a screen (typically 0.132"), and dried in a fluid bed drier until loss on drying is less than 0.2-0.5% w/w.

TABLE 4

% Composition of Form V or Form F of Desvenlafaxine Succinate (50%, w/w) Granular Concentrate

| | Granular concentrate batch # | | |
|---|---|---|---|
| | 1 | 2 | 3 |
| Form V or Form F of desvenlafaxine succinate | 100 | 100 | 100 |
| Lactose anhydrous | 50 | | 10 |
| Dicalcium phosphate | | 50 | 20 |
| Sodium starch glycolate | 10 | 10 | 10 |

TABLE 4-continued

% Composition of Form V or Form F of Desvenlafaxine Succinate (50%, w/w) Granular Concentrate

| | Granular concentrate batch # | | |
|---|---|---|---|
| | 1 | 2 | 3 |
| Hydroxypropyl methyl cellulose (HPMC) | | | 40 |
| Pregelatinized starch | 10 | 20 | 10 |
| Microcrystalline cellulose | 30 | 20 | 10 |
| Purified water* | | | |

*Water was removed during the process

The dried granules were passed a screen (typically 0.039") and blended using a tumble blender for 10 minutes at 12 rpm.

B: Preparation of Tablet Core Comprising Form V or Form F of Desvenlafaxine Succinate The concentrated granules are placed into a tumble blender. About two thirds of the lactose is screened and added to the blender, and blended for ten (10) minutes. The microcrystalline cellulose, sodium starch glycollate, magnesium stearate and remaining lactose are screened and added to the blender. The mixtures are blended together for ten (10) minutes. The blended material was compressed on a Kikusui Libra tablet compression machine to a target weight of 300 mg for the 50 mg and 100 mg tablets.

C: Preparation of Coated Tablet Comprising Form V or Form F of Desvenlafaxine Succinate The tablet cores are then transferred to a tablet-coating machine (pan coater). The tablet bed was pre-heated with warm air (approximately 60° C.). The pan speed

TABLE 5

% Composition of Tablet Core (quantity, mg per tablet)

| | Formulation batch# | | |
|---|---|---|---|
| | 1 | 2 | 3 |
| Dosage strength | 50 mg | 100 mg | 100 mg |
| Form V or Form F of desvenlafaxine succinate concentrate granules | 100 | 200 | 200 |
| Lactose anhydrous | 150 | 10 | 10 |
| Microcrystalline cellulose | 47 | 87 | 87 |
| Magnesium stearate | 3 | 3 | 3 |
| Total weight | 196 | 196 | 196 |
| Coating material | 4.0 | 4.0 | 4.0 |
| Total weight of coated tablet | 300.0 | 300.0 | 300.0 | was adjusted to 5-9 RPM before starting the spray cycle. The spray cycle was activated. The exhaust temperature was maintained between 40° C. and 50° C. throughout the cycle. After the proper amount of solution was applied, the coated tablets were dried for approximately two (2) minutes. Steps were repeated for all pans to coat all tablets in the batch and film coated until the tablet weight has increased by 2.0% to 3.5%. All tablets were packaged in plastic bottles with desiccants, and the bottles were heat sealed, then placed under the stress condition.

Example 10

Stability Studies

The stability of Form V or Form F of desvenlafaxine succinate bulk material and tablets is assessed by storing samples for up to 6 or 12 weeks at 25° C./60% RH or 40° C./75% RH. Changes are monitored using a stability-indicating HPLC method. Results were calculated by normalized peak area (npa). Degradants are identified by comparison of their relative retention times against impurity standards.

(i) Polymorph Form V or Form F of Desvenlafaxine Succinate Bulk Material

Polymorph Form V or Form F of desvenlafaxine succinate bulk material was stable with respect to polymorph stability as well as formation of known and unknown degradants for over 3 to 6 months when stored under normal conditions of temperature and humidity. Similarly, 2 months polymorph and chemical stability of Form V or Form F was demonstrated at elevated temperatures and humidity (40° C./75%).

ii) Tablets Comprising Form V or Form F of Desvenlafaxine Succinate

Tablets comprising polymorph Form V or Form F of desvenlafaxine succinate was stable with respect to the formation of known and unknown degradants for over 3 to 6 months when stored under normal conditions of temperature and humidity. Similarly, 2 months polymorph and chemical stability of Form V or Form F was demonstrated at elevated temperatures and humidity (40° C./75%).

We claim:

1. Polymorph Form V of desvenlafaxine succinate.

2. The polymorph Form V of claim 1, characterized as having an X-ray diffraction pattern with characteristic peaks (expressed in 2θ±0.2° 2θ) at one or more of the following positions: 5.08, 10.20, 10.70, 13.10, 14.58, 15.12, 16.62, 17.10, 17.58, 19.14, 20.06, 20.56, 21.62, 22.32, 23.26, 23.74, 25.16, 25.80, 27.12, 27.84, 30.38 or 33.72.

3. The polymorph Form V of claim 1, characterized as having X-ray powder diffraction pattern substantially the same as that shown in FIG. 1.

4. The polymorph Form V of claim 1, characterized as having two endothermic peaks in differential scanning calorimetry (DSC) at about 115-125° C. and about 136-141° C.

5. Polymorph Form F of desvenlafaxine succinate.

6. The polymorph Form F of claim 5, characterized as having X-ray diffraction pattern with characteristic peaks (expressed in 2θ±0.2° 2θ) at one or more of the following positions: 5.22, 10.14, 10.60, 11.70, 13.06, 14.20, 14.52, 15.04, 16.54, 17.04, 17.48, 19.36 19.96, 20.68, 21.52, 22.20, 23.22, 23.74, 25.04, 25.74, 26.98, 27.48, 27.78, 28.66 or 30.16.

7. The polymorph Form F of claim 5, characterized as having X-ray powder diffraction pattern substantially the same as that shown in FIG. 7, FIG. 9 or FIG. 11.

8. The polymorph Form F of claim 5, characterized as having a characteristic endothermic peak in differential scanning calorimetry (DSC) at about 138-143° C.

9. A pharmaceutical composition comprising Form V or Form F of desvenlafaxine succinate and at least one or more pharmaceutically acceptable carrier, excipient, diluent, additive, filler, lubricant or binder.

10. The pharmaceutical composition according to claim 9, wherein the composition is formulated for oral administration.

11. The pharmaceutical composition according to claim 9, wherein the dosage form is a tablet or a capsule.

12. The pharmaceutical composition according to claim 9 or claim 11, wherein the dosage form is a delayed, sustained or extended release formulation.

13. The pharmaceutical composition according to claim 12, wherein the rate controlling excipient is selected from a group consisting of hydroxyalkyl celluloses, poly(ethylene) oxides, alkyl cellulose, carboxymethyl celluloses, carboxyvinyl polymers, hydrophilic cellulose derivatives, polyethylene glycol derivatives or polyvinylpyrrolidone derivatives.

14. A composition comprising (a) polymorph Form V or Form F of desvenlafaxine succinate and (b) a crystalline, hydrate, solvate, amorphous, polymorph Form I, Form II, Form III, Form VI or other polymorphic forms of desvenlafaxine succinate other than Form V or Form F, wherein the total weight of desvenlafaxine succinate in the composition is the sum of (a) and (b).

15. The composition of claim 14, wherein the composition comprises less than 0.1% to at least 99.9% by weight of polymorph Form V or Form F based on the total weight of desvenlafaxine succinate in the composition.

16. The composition of claim 14, wherein the composition comprises less than 0.1% by weight of polymorph Form V or Form F based on the total weight of desvenlafaxine succinate in the composition.

17. The composition of claim 14, wherein the composition comprises less than 2% by weight of polymorph Form V or Form F based on the total weight of desvenlafaxine succinate in the composition.

18. The composition of claim 14, wherein the composition comprises at least 50% by weight of polymorph Form V or Form F based on the total weight of desvenlafaxine succinate in the composition.

19. The composition of claim 14, wherein the composition comprises at least 80% by weight of polymorph Form V or Form F based on the total weight of desvenlafaxine succinate in the composition.

20. The composition of claim 14, wherein the composition comprises at least 95% by weight of polymorph Form V or Form F based on the total weight of desvenlafaxine succinate in the composition.

21. The composition of claim 14, wherein the composition comprises at least 99.9% by weight of polymorph Form V or Form F based on the total weight of desvenlafaxine succinate in the composition.

* * * * *